United States Patent [19]

Dieterich

[11] 4,189,562
[45] Feb. 19, 1980

[54] POLYHYDROXY COMPOUNDS CONTAINING URETHANE ARYL SULFONIC ACID HYDROXYALKYL ESTER GROUPS

[75] Inventor: Dieter Dieterich, Leverkusen, Fed. Rep. of Germany

[73] Assignee: Bayer Aktiengesellschaft, Leverkusen, Fed. Rep. of Germany

[21] Appl. No.: 929,617

[22] Filed: Jul. 31, 1978

[30] Foreign Application Priority Data

Mar. 8, 1977 [DE] Fed. Rep. of Germany ....... 2735032

[51] Int. Cl.$^2$ ............................................. C08L 81/00
[52] U.S. Cl. ................. 528/75; 260/456 A; 528/76; 528/77; 528/391
[58] Field of Search .................... 528/391, 76, 77, 75; 260/456 A

[56] References Cited

U.S. PATENT DOCUMENTS 3,892,720   7/1975   Jahnke .............................. 260/456 A
3,959,333   5/1976   Jahnke ................................. 528/391

OTHER PUBLICATIONS

Chem. Absts. 86:6304z, 1977.

*Primary Examiner*—Maurice J. Welsh
*Attorney, Agent, or Firm*—Gene Harsh; Joseph C. Gil; R. Brent Olson

[57] ABSTRACT

The instant invention is directed to polyhydroxyl compounds containing at least two hydroxyl groups and at least one sulfonic acid ester group and having an average molecular weight of from 300 to 12,000, wherein at least one hydroxyl containing compound contains a urethane aryl sulfonic acid hydroxyalkyl ester group. The invention also relates to a process for producing these compounds and the product by the process.

20 Claims, No Drawings

POLYHYDROXY COMPOUNDS CONTAINING URETHANE ARYL SULFONIC ACID HYDROXYALKYL ESTER GROUPS

BACKGROUND OF THE INVENTION

It is known that polyurethanes may be produced by reacting polyisocyanates with compounds containing from 2 to 6 OH-groups and having a molecular weight of from 62 to about 10,000. Examples of these polyhydroxy compounds are difunctional and more highly functional alcohols, such as ethylene glycol, diethylene glycol, hexane diol, glycerol and trimethylol propane, and also relatively high molecular weight polyethers, polythioethers, polyesters and polyacetals. The relatively high molecular weight polyhydroxy compounds are produced in known manner from low molecular weight units.

In these polyhydroxy compounds, the various OH-functions are generally equivalent in regard to the reactivity thereof and the distance thereof from any branching center present. Exceptions are low molecular weight alcohols containing primary and secondary hydroxy groups, such as glycerol. Although, in the case of relatively high molecular weight polyethers and polyesters, both primary and secondary OH-groups are also present in many cases, the distribution thereof is statistical so that it is not possible to synthesize polymers having a defined structure on account of this difference in reactivity. The chain length distributions in branched polyethers and polyesters are also statistical.

It is also known that the above-mentioned polyhydroxy compounds may be extended by a sub-molar quantity of a polyisocyanate to form OH-prepolymers. Although branching occurs in the case of trifunctional isocyanates, the reactivity of the OH-groups and the chain length distribution are again statistical.

In addition, the separate production of OH-prepolymers for the subsequent production of polyurethanes is generally not advisable because the same polyurethane structures are formed where production is carried out by the one-shot process or via NCO-prepolymers.

The production of polyurethanes and, in particular, the production of sterically cross-linked polyurethanes requires polyhydroxy compounds which contain OH-groups of different reactivity and chain branches of different length. It would be advantageous, for example, if trifunctional polyhydroxy compounds were available which contained two OH-groups of high reactivity at the ends of the main chain and an OH-function of reduced reactivity in as short a side chain as possible. Such a structure could be expected to give a polymer having particularly favorable mechanical properties. It is also desirable to be able to use polyhydroxy compounds which give polyurethanes having improved flame resistance. Furthermore, there is a need for OH-prepolymers which, in the event of hydrolytic degradation, do not form toxic aromatic diamines. The present invention provides a solution to these problems.

DESCRIPTION OF THE INVENTION

The instant invention is directed to a process wherein polyhydroxy compounds are reacted with an equivalent quantity of isocyanato- mono- or poly-sulfonic acids. The products formed are subsequently reacted with oxiranes or oxetanes. The reaction products will be a mixture of hydroxyl containing compounds. Some of the hydroxyl containing compounds will also contain a urethane aryl sulfonic acid hydroxy alkyl ester group. The instant invention is directed to the process, the mixture of compounds produced, specific compounds within the mixture, and the products by this specific process.

The instant invention is also directed to a process wherein polyhydroxyl compounds are reacted with a sub-molar quantity of aromatic isocyanatosulfonic acids, optionally in admixture with conventional polyisocyanates. The reaction products are subsequently reacted with oxiranes or oxetanes. In these polyhydroxyl compounds, the hydroxyl group formed by the reaction of the sulfonic acid group with the cyclic ether is situated on a short side chain. The instant invention is also directed to this process, the mixture of products produced, specific compounds within the mixture, and the products by this specific process.

According to the present invention, preferred compounds are compounds which have an average molecular weight of from 300 to 12,000 and which are characterized by at least one OH-functional long chain containing from 6 to 400 chain members, preferably from 20 to 300 chain members, and at least one OH-functional short chain having 2 or 3 chain members which is attached to a branching point through a sulfonic acid ester residue and at least one tri- or higher functional aryl radical as the branching point.

The compounds preferably contain at least one structural unit corresponding to the following general formula:

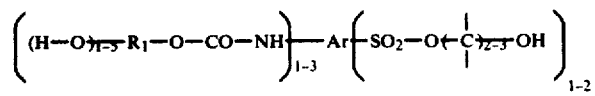

wherein
R$_1$ represents a residue from a material having from 2 to 6 OH groups, for example a polyester, polyether, polythioether or polyester amide; and
Ar represents a polyfunctional residue of an aromatic isocyanate; in particular at least one structural unit corresponding to the following general formula:

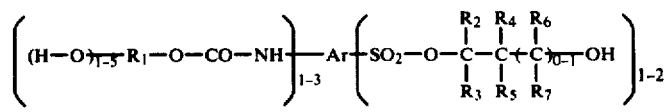

wherein
R$_1$ and Ar are as defined above;

$R_2$ and $R_4$ represent H, $C_1$-$C_8$ alkyl, $C_6$-$C_{14}$ aryl, a residue of an epoxide (preferably—$CH_2$—O—$R_8$), —$CH_2$—X, $CH_2$—O—CO—$R_9$ or an aliphatic $C_1$-$C_8$ alkyl radical containing further epoxide groups;

$R_3$, $R_5$, $R_6$ and $R_7$ represent H, $C_1$-$C_8$ alkyl or $C_6$-$H_{14}$ aryl $R_8$ and $R_9$ represent $C_1$-$C_8$ alkyl or $C_6$-aryl; and X represents OH, Cl, Br or CN.

Preferred are compounds corresponding to the following general formulae:

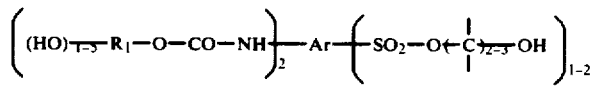

in particular

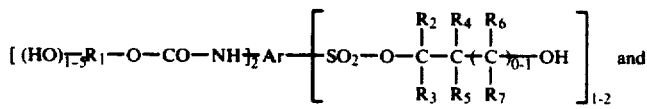

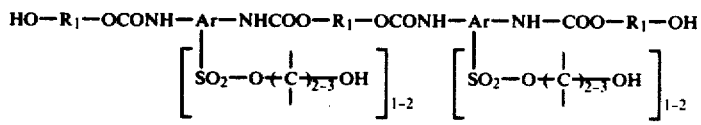

in particular

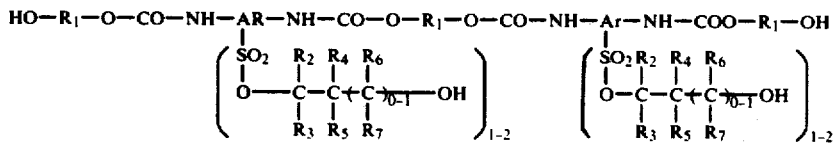

wherein $R_1$, $R_2$, $R_3$, $R_4$, $R_5$, $R_6$, $R_7$ and Ar are as defined above. Most preferably $R_3$ and $R_5$ (in case of an oxirane) or $R_2$, $R_3$, $R_6$ and $R_7$ (in case of an oxetane) represent hydrogen.

The present invention also relates to a process for the production of compounds containing at least two hydroxyl groups and at least one sulfonic acid ester group and having an average molecular weight of from 300 to 12,000, in which at least one of the hydroxyl containing compounds also contains a urethane aryl sulfonic acid hydroxyalkyl ester group, characterized in that compounds containing at least two hydroxy groups and having a molecular weight of from 62 to 10,000 are reacted at from 0° to 190° C. with isocyanato-sulfonic acid and then with oxiranes and/or oxetanes. The equivalent ratio of the total quantity of isocyanate groups (including any isocyanate groups present in dimerized form) to sulfonic acid groups is from 0.5:1 to 50:1. The equivalent ratio of the sum of hydroxyl groups in the compounds containing at least two hydroxyl groups and the sulfonic acid groups to NCO groups is from 1.5:1 to 30:1. The equivalent ratio of the oxirane or oxetane groups to sulfonic acid groups is from 0.2:1 to 5:1.

Furthermore, the present invention also relates to the use of the compounds as reaction component for polyisocyanates in the production of polyaddition products or polycondensation products.

The new compounds yield a number of advantageous properties over the previously known polyhydroxy compounds:

1. They are strongly polar in character, have an extremely low vapor pressure and are highly compatible with a number of polar and apolar media and reactants.

2. Depending upon the chemical constitution of the oxirane or oxetane used, the reactivity of the OH-group attached to the branching point through a short side chain may be controlled as required. The reactivity of this OH-group may be higher than, substantially equal to or even lower than that of the OH-group introduced through the polyhydroxy compound.

3. The functionality of the polyhydroxy compounds may be increased as required, for example from 2 to 2.1 or even from 2 to 3 or 2 to 4, in dependence upon the quantity of isocyanatosulfonic acid used.

4. The hydrophilicity and acidity of the products may be controlled within wide limits, depending upon the nature and quantity of the oxirane or oxetane used. Where the sulfonic acid groups are completely reacted with oxiranes or oxetanes, substantially hydrophobic polyhydroxy compounds are obtained.

5. The hydrolytic degradation of the products results in the formation of non-toxic polyaminosulfonic acids.

6. The use of the compounds in the production of, for example, polyurethanes, leads to polymers having improved fire resistance.

The products and the chain segments obtained from them in the synthesis of polyurethanes are not readily obtainable by other methods because the direct reaction of isocyanatoaryl sulfonic acids or NCO-prepolymers obtained therefrom with oxiranes or oxetanes gives different products and chain segments having a different structure. The compounds according to the present invention preferably contain at least one segment which represents a from 2-functional to 6-functional residue of a polyether, polythioether, polyester or polyester amide.

In the practical application of the invention, some of the OH-groups of the polyhydroxy compounds used as starting material are normally subjected in a first reaction step to addition with the NCO-groups and any uretdione groups of the isocyanatoaryl sulfonic acid which may be present to form relatively high molecular weight new polyhydroxy compounds which initially contain some urethane groups and one or more free sulfonic acid groups. The sulfonic acid group is subsequently esterified by the oxirane or oxetane added, resulting in the formation of hydroxyalkyl sulfonic acid ester groups.

The starting materials may be any of the compounds containing at least two hydroxy groups and having a molecular weight of from 62 to 10,000 which are normally used in polyurethane chemistry. Thus, suitable starting materials include low molecular weight glycols, polyesters, polyethers, polyester amides, OH-functional oligomers, polymers. Examples of polymers are those based on butadiene and polyethers grafted by vinyl monomers. Polyethers of the type which contain other polymers in dispersion, such as polyureas, urea resins, polyhydrazodicarbonamides or vinyl polymers may also be used. Examples of suitable hydroxy functional compounds are given below.

The polyesters containing hydroxyl groups may be reaction products of polyhydric, preferably dihydric and, optionally, even trihydric, alcohols with polybasic, preferably dibasic, carboxylic acids. Instead of using the free polycarboxylic acids, it is also possible to use the corresponding polycarboxylic acid anhydrides or corresponding polycarboxylic acid esters of lower alcohols or mixtures thereof for producing the polyesters. The polycarboxylic acids may be aliphatic, cycloaliphatic, aromatic and/or heterocyclic. The acids may optionally be substituted, for example by halogen atoms, and/or they may be unsaturated. Examples of suitable polycarboxylic acids include: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dibasic and tribasic fatty acids, such as oleic acid, optionally in admixture with monobasic fatty acids, terephthalic acid dimethyl ester and terephthalic acid-bis-glycol ester. Suitable polyhydric alcohols include, for example, ethylene glycol, 1,2- and 1,3-propylene glycol, 1,4- and 2,3-butylene glycol, 1,6-hexane diol, 1,8-octane diol, neopentyl glycolcyclohexane dimethanol (1,4-bis-hydroxymethyl cyclohexane), 2-methyl-1,3-propane diol, glycerol, trimethylol propane, 1,2,6-hexane triol, 1,2,4-butane triol, trimethylol ethane, pentaerythritol, quinitol, mannitol, sorbitol, methyl glycoside, diethylene glycol, triethylene glycol, tetraethylene glycol, polyethylene glycols, dipropylene glycol, polypropylene glycols, dibutyl glycol and polybutylene glycols. In addition to hydroxyl groups the polyesters may also contain terminal carboxyl groups. Polyesters of lactones, for example ε-caprolactone, or hydroxy carboxylic acids, for example ω-hydroxy caproic acid, may also be used.

The polyethers containing hydroxyl groups, preferably two hydroxyl groups, which may be used are also known and are obtained, for example, by the polymerization of epoxides, such as ethylene oxide, propylene oxide, butylene oxide, tetrahydrofurane, styrene oxide, epichlorohydrin or 1,1,1-trichloroacetene-3,4-oxide. These epoxides may be polymerized on their own in the presence of $BF_3$, or by addition of these epoxides, if desired in admixture or successively, with starter components containing reactive hydrogen atoms, such as water, alcohols or amines. Examples of such alcohols and amines are ethylene glycol, 1,3- or 1,2-propylene glycol, 4,4'-dihydroxy diphenyl propane, aniline, and the like.

Polyethers modified by vinyl polymers of the type obtained by polymerizing styrene, acrylonitrile in the presence of polyethers (U.S. Pat. Nos. 3,383,351; 3,304,273; 3,523,093 and 3,110,695; German Pat. No. 1,152,536) are also suitable. The polyethers of relatively high functionality which may be proportionately used are similarly formed in known manner by the alkoxylation of starter molecules of relatively high functionality, such as ammonium, ethanolamine, ethylene diamine or sucrose.

Among the polythioethers, particularly preferred are the condensation products of thiodiglycol on its own and/or with other glycols, dicarboxylic acids, formaldehyde, amino-carboxylic acids or amino alcohols. Depending upon the co-components, the products in question are polythio mixed ethers, polythioether esters or polythioether ester amides.

Suitable polyacetals include, for example, the compounds obtainable from the reaction of glycols, such as diethylene glycol, triethylene glycol, 4,4'-dioxethoxy diphenyl methyl methane and hexane diol, with formaldehyde. Polyacetals suitable for use in accordance with the present invention may also be obtained by the polymerization of cyclic acetals.

Suitable polycarbonates containing hydroxyl groups are known and may be obtained, for example, by reacting diols such as 1,3-propane diol, 1,4-butane diol and/or, 1,6-hexane diol, diethylene glycol, triethylene glycol and tetraethylene glycol, with diaryl carbonates (for example diphenyl carbonate) or with phosgene.

The polyester amides and polyamides include, for example, the predominantly linear condensates obtained from polybasic saturated and unsaturated carboxylic acids or the anhydrides thereof and polyhydric saturated and unsaturated aminoalcohols, diamines, polyamines and mixtures thereof. Polyhydroxyl compounds already containing urethane or urea groups may also be used.

It is also possible to use polyhydroxyl compounds containing high molecular weight polyadducts or polycondensates in finely dispersed or dissolved form. Such modified polyhydroxyl compounds are obtained by directly carrying out polyaddition reactions (for example reactions between polyisocyanates and amino-functional compounds) or polycondensation reactions (for example between formaldehyde and phenols and/or amines) in situ in the above-mentioned compounds containing hydroxyl groups. Such processes are described in German Auslegeschriften 1,168,075 and 1,260,142 and in German Offenlegungsschriften 2,324,134; 2,423,984; 2,512,385; 2,513,815; 2,550,796; 2,550,797; 2,550,833 and 2,550,662. However, it is also possible, according to U.S. Pat. No. 3,869,413 or German Offenlegungsschrift 2,550,860, to mix an aqueous polymer dispersion with a polyhydroxyl compound and subsequently to remove the water from the mixture.

Low molecular weight glycols which may be reacted with isocyanatosulfonic acids either alone or in admixture with the above-mentioned relatively high molecular weight polyhydroxy compounds include, for example, ethylene glycol, diethylene glycol, triethylene glycol, tetraethylene glycol, propylene glycol, oligopropylene glycols, 1,3-propylene glycol, butane diol, hexane diol, 2-ethylhexane diol, octane diol, glycerol, trimethylol propane and dodecane diol. Amino alcohols, such as ethanolamine, propanolamine and diethanolamine, may also be used with the proviso that all the amino groups present are reacted with isocyanate groups. Monoamines, diamines or polyamines and water may also be used in small quantities. In addition to OH-groups, the products obtained after the reaction may contain small quantities of carboxyl groups or mercapto groups.

The sulfonation products of any known aromatic polyisocyanates may be used as the isocyanatoaryl sulfonic acids in the process. The following are examples of these aromatic polyisocyanates which may be used in the form of the sulfonation products thereof: 4,4'-stilbene diisocyanate, 4,4'-dibenzyl diisocyanate; 3,3'- and 2,2'-dimethyl-4,4'-diisocyanatodiphenylmethane; 2,3,2',5'-tetramethyl-4,4'-diisocyanatodiphenylmethane; 3,3'-dimethoxy-4,4'-diisocyanatodiphenylmethane; 3,3'-dichloro-4,4'-diisocyanatodiphenyl methane; 4,4'-diisocyanatodiphenyl cyclohexyl methane; 4,4'-diisocyanatobenzophenone; 4,4'-diisocyanatodiphenyl sulphone; 4,4'-diisocyanatodiphenyl ether; 4,4'-diisocyanato-3,3'-dibromodiphenyl methane; 4,4'-diisocyanato-3,3'-diethyl diphenyl methane; 4,4'-diisocyanatodiphenyl-1,2-ethylene; 4,4'-diisocyanatodiphenyl sulphide; 1,3- and 1,4-phenylene diisocyanate; 2,4- and 2,6-tolylene diisocyanate and mixtures of these isomers; diphenyl methane-2,4'- and/or -4,4'-diisocyanate; naphthylene-1,5-diisocyanate, and triphenylmethane-4,4',4"-triisocyanate. Additional examples are polyphenyl polymethylene polyisocyanates of the type obtained by condensing aniline with formaldehyde, followed by phosgenation, as described in British Pat. Nos. 874,430 and 848,671; polyisocyanates containing carbodiimide groups as described in German Pat. No. 1,092,007; diisocyanates of the type described in U.S. Pat. No. 3,492,330; polyisocyanates containing allophanate groups as described in British Pat. No. 994,890, Belgian Pat. No. 761,626 and Published Dutch Patent Application No. 7,102,524; polyisocyanates containing isocyanurate groups as described in German Pat. Nos. 1,022,789; 1,222,067 and 1,027,394 and German Offenlegungsschriften Nos. 1,929,034 and 2,004,048; polyisocyanates containing acylated urea groups according to German Pat. No. 1,230,778; and, polyisocyanates containing biuret groups as described in German Pat. No. 1,101,394, British Pat. No. 889,050 and French Pat. No. 7,017,514. It is also possible to use the distillation residues containing isocyanate groups which are obtained in the commercial production of isocyanates, optionally in solution in one or more of the above-mentioned polyisocyanates. Mixtures of the above-mentioned polyisocyanates may also be used.

It is also possible to use phosgenation products of condensates of aniline and aldehydes or ketones, such as acetaldehyde, propionaldehyde, butyraldehyde, acetone, and methylethyl ketone. Phosgenation products of condensates of anilines alkyl-substituted on the nucleus, particularly toluidines, with aldehydes or ketones, such as formaldehyde, acetaldehyde, butyraldehyde, acetone and methylethyl ketone may also be used.

Reaction products of the above-mentioned aromatic polyisocyanates with from 0.2 to 50 mol % of polyols are also suitable, provided that the viscosity of the thus-obtained reaction products does not exceed 50,000 cP at 25° C. and the NCO-content of the reaction products amounts to at least 6%, by weight. Suitable polyols for modifying the starting materials include, in particular, polyether and/or polyester polyols having molecular weights of from 200 to 6000, preferably from 300 to 4000, and low molecular weight polyols having molecular weights of from 62 to 200, of the type known and/or commonly used in polyurethane chemistry. Examples of such low molecular weight polyols include ethylene glycol, propylene glycol, glycerol, trimethylol propane and 1,4,6-hexane triol.

Particularly preferred isocyanatoaryl sulfonic acids are the sulfonation products of 2,4-tolylene diisocyanate and mixtures of 2,4- and 2,6-tolylene diisocyanate; and, sulfonation products of the diisocyanates and polyisocyanates obtained by phosgenating aniline/formaldehyde condensates. These mixtures contain, in particular, 4,4'-diisocyanatodiphenyl methane and 2,4'-diisocyanatodiphenyl methane and higher nuclear homologues of these products. Basically, the isocyanatoaryl sulfonic acids may be produced using any sulfonating agents. Suitable sulfonating agents include, for example, sulfur trioxide, oleum, sulfuric acid and complexes of sulfur trioxide with Lewis bases which contain oxygen, nitrogen or phosphorus atoms. However, it is also possible to use other known sulfonating agents, such as chlorosulfonic acid and acyl sulfates, for example acetyl sulfate, or reaction products of acid anhydrides with sulfuric acid or oleum. In general, secondary reactions, for example urea or biuret formation or the partial conversion of isocyanate groups into carbamic acid chloride groups or acyl amide groups, are of no significance. This is the case particularly in the production of only partially sulfonated isocyanates, so that in such cases sulfuric acid, chlorosulfonic acid or acetyl sulfate, for example, may readily be used. By contrast, for producing highly sulfonated polyisocyanates, it is preferred to use sulfur trioxide or its complexes as in German Offenlegungsschrift No. 2,510,693. Aromatic polyisocyanatoaryl sulfonic acids based on tolylene diisocyanate or diphenyl methane diisocyanate which contain urea or biuret groups are also preferred.

Solutions and dispersions of isocyanatoaryl sulfonic acids in non-sulfonated liquid polyisocyanates are particularly preferred. Such products are obtained, for example, in the partial sulfonation of aromatic polyisocyanates. In general, suspensions are obtained in the partial sulfonation of chemically uniform diisocyanates or binary isomer mixtures, whereas homogeneous solutions are formed in the partial sulfonation of multi-component mixtures. Basically, it does not matter whether solutions or suspensions are used for the process. It is particularly preferred to use partially sulfonated polyisocyanate mixtures of the type which are obtained by phosgenating aniline/formaldehyde condensates and which are described in German Offenlegungsschriften Nos. 2,227,111; 2,359,614 and 2,359,615. Suspensions of diisocyanatotoluene sulfonic acid dimers and diisocyanatodiphenyl methane sulfonic acid dimers in diisocyanatotoluene or diisocyanatodiphenyl methane are also particularly preferred.

The isocyanatoaryl sulfonic acids used in the process and mixtures thereof with non-sulfonated aromatic polyisocyanates are produced by conventional processes or modified processes such as are described in the abovementioned publications or in U.S. Pat. No. 3,826,769. The process according to British Pat. No. 1 494 467 (U.S. Ser. No. 848,969) and German Offenlegungsschrift No. 26 15 876 (U.S. Ser. No. 782,642) are also suitable for the production of isocyanatoaryl sulphonic acids suitable for use in the present invention.

It is also possible to use solutions or suspensions of the exemplified isocyanatoaryl sulfonic acids in aliphatic polyisocyanates, such as tetramethylene diisocyanate or hexamethylene diisocyanate and/or in cycloaliphatic or mixed aliphatic-cycloaliphatic polyisocyanates, such as 4,4'-diisocyanato-dicyclohexyl methane, 2,4- and 2,6-diisocyanatohexahydrotoluene or 1-isocyanato-3,3,5-trimethyl-5-isocyanatomethyl cyclohexane. In cases where it is desired to reduce the NCO-functionality of the process products, it is also possible to use solutions or suspensions of the isocyanatoaryl sulfonic acids in aromatic, aliphatic or cycloaliphatic monoisocyanates. Examples of monoisocyanates include phenyl isocyanates, octyl isocyanate, n-hexyl isocyanate, 6-chlorohexyl isocyanate, cyclohexyl isocyanate or methoxymethyl isocyanate. It is also possible to use sulfonated aromatic monoisocyanates such as phenyl isocyanate, as the isocyanatoaryl sulfonic acid in combination with nonsulfonated polyisocyanates of the type noted above.

The nature of the isocyanates used in the process and the quantitative ratios in which they are used and also the degree of sulfonation are frequently selected in such a way that (in case isocyanates with only one sulfonic acid group are used) the equivalent ratio of isocyanate groups, optionally present in partially dimerized form, to sulfonic acid groups amounts to more than 1:1, i.e. in particular from 1.05:1 to 50:1, preferably from 2:1 to 30:1. A ratio of from 2:1 to 12:1 is especially preferred.

Another group of preferred isocyanatosulfonic acids are the aromatic monoisocyanates, diisocyanates or polyisocyanates which contain more than one sulfonic acid group and, in particular, 2 or 3 sulfonic acid groups. Such isocyanatopolysulfonic acids are described in German Offenlegungsschrift No. 2,615,876. The preferred ratio of isocyanate groups to sulfonic acid groups in this case is from 0.5:1 to 1.2:1.

The oxiranes used in the process according to the present invention may be any organic compounds which contain at least one epoxide group and which, in addition, may optionally be substituted by isocyanate or hydroxyl groups, but are otherwise substantially inert under the reaction conditions under which the oxirane-sulfonic acid addition takes place. Monoepoxides having molecular weights of from 44 to 400 which correspond to this definition are preferably used in the process. Examples of suitable monoepoxides include ethylene oxide, propylene oxide, butene-1,2-oxide, butene-2,3-oxide, 1,4-dichlorobutene-2,3-oxide, styrene oxide, 1,1,1-trichloropropene-2,3-oxide, 1,1,1-trichlorobutene-3,4-oxide, 1,4-dibromobutene-2,3-oxide, epichlorhydrin, epibromohydrin, glycidyl, glycerol monoglycidyl ether, isobutene oxide, p-glycidyl styrene, N-glycidyl carbazole, cyanoethyl glycidyl ether, trichloroethyl glycidyl ether, chloroethyl glycidyl ether, bromoethyl glycidyl ether, vinyl oxirane, 3,4-dichlorobutene-1,2-oxide, 2-(1-chlorovinyl)-oxirane, 2-chloro-2-vinyl oxirane, 2,3-epoxypropyl phosphonic acid diethyl ester, 3,4-bis-hydroxy butene-1,2-oxide, 2-methyl-2-vinyl oxirane and 2-(1-methylvinyl)-oxirane. Esters of glycidol with monocarboxylic acids are also suitable. Examples of such esters are glycidyl acetate, glycidyl chloroacetate, glycidyl dichloroacetate, glycidyl trichloroacetate, glycidyl bromoacetate, glycidyl acrylate, glycidyl methacrylate, glycidyl caproate, glycidyl octoate, glycidyl dodecanoate, glycidyl oleate, and glycidyl stearate. Ethers of glycidol, for example with phenol and substituted, particularly halogenated, phenols, are also suitable. The reaction products of hydroxy oxiranes, particularly of glycidol, with aliphatic, and aromatic monoisocyanates and polyisocyanates are also suitable.

In order to increase molecular weight and functionality, it is also possible to use diepoxides and polyepoxides either individually or in combination with the abovementioned monoepoxides. Such difunctional and polyfunctional epoxides include the epoxidation products of aliphatic and cycloaliphatic diolefins, such as diepoxy butane, diepoxy hexane, vinyl cyclohexene dioxide, dicyclopentadiene dioxide, limonene dioxide, dicyclopentadiene dioxide, ethylene glycol-bis-(3,4-epoxy-tetrahydrodicyclopentadien-8-yl)-ether, (3,4-epoxytetrahydrodicyclopentadien-8-yl)-glycidyl ether. Also included are epoxidized polybutadienes or copolymers or butadiene with ethylenically unsaturated compounds, such as styrene or vinyl acetate, compounds containing two epoxy cyclohexyl radicals, such as diethylene glycol-bis-(3,3-epoxy-cyclohexane carboxylate), bis-3,4-(epoxy-cyclohexylmethyl)-succinate, 3,4-epoxy-6-methyl cyclohexylmethyl-3',4'-epoxy-6'-methyl cyclohexane carboxylate and 3,4-epoxy hexahydrobenzal-3',4'-epoxy cyclohexane-1',1'-dimethanol.

Other materials which may be used in the present invention are polyglycidyl esters such as those obtained by reacting a dicarboxylic acid or cyanuric acid with epichlorhydrin or dichlorhydrin in the presence of an alkali. Such polyesters may be derived from aliphatic dicarboxylic acids, such as succinic acid or adipic acid, and, in particular, from aromatic dicarboxylic acids, such as phthalic acid or terephthalic acid. Diglycidyl adipate, diglycidyl phthalate and triglycidyl isocyanurate may be mentioned in this connection.

Polyglycidyl ethers such as those obtained by etherifying a dihydric or polyhydric alcohol, a diphenol or a polyphenol with epichlorhydrin or dichlorhydrin in the presence of an alkali are preferably used. These compounds may be derived from glycols, such as ethylene glycol, diethylene glycol, triethylene glycol, 1,3-propylene glycol, 1,4-butane diol, 1,5-pentane diol, 1,6-hexane diol, 2,4,6-hexane triol and glycerol. In particular, they may be derived from diphenols or polyphenols, such as resorcinol, pyrocatechol, hydroquinone, phenolphthalein, phenol/formaldehyde condensation products of the novolak type, 1,4-dihydroxy naphthalene, dihydroxy-1,5-naphthalene, bis-(hydroxy-4-phenyl)-methane, tetrahydroxyphenyl-1,1,2,2,-ethane, bis-(hydroxy-4-phenyl)-methyl-phenyl methane, the bis-(hydroxy-4-phenyl)-tolyl methanes, dihydroxy-4,4'-diphenyl, bis-(hydroxy-4-phenyl)-sulfone and, in particular, bis-(hydroxy-4-phenyl)-2,2-propane or the condensation products of a phenol with an aldehyde or a ketone. In the latter case, the products in question are epoxy resins containing two or more epoxy groups and, optionally, free hydroxyl groups. Particularly suitable epoxy resins of this type are the epoxy resins which are produced from polyphenols and which are marketed under the trade name of "NOVOLAK" resins, the polycondensation products of a phenol with formol. The epoxy resins obtained correspond to the following general formula:

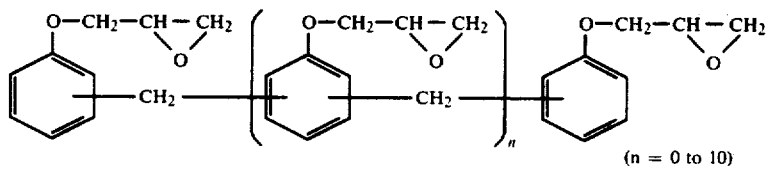

(n = 0 to 10)

Other suitable polyglycidyl ethers are polyglycidyl ethers of diphenols obtained by esterifying 2 mols of the sodium salt of an aromatic oxycarboxylic acid with 1 mol of a dihalogen alkane or dihalogen dialkyl ether (see, e.g., British Pat. No. 1,017,612) and polyphenols obtained by condensing phenols and long-chain halogen paraffins containing at least two halogen atoms (see, e.g., British Pat. No. 1,024,288). Reference is also made to polyepoxide compounds based on aromatic amines and epichlorhydrin, for example N-di-(2,3-epoxy-propyl)-aniline, N,N'-dimethyl-N,N'-diepoxypropyl-4,4'-diaminodiphenyl methane, N,N'-tetraepoxypropyl-4,4'-diaminodiphenyl methane and N-diepoxypropyl-4-aminophenyl glycidol ether (see, e.g., British Pat. Nos. 772,830 and 816,923). It is also possible to use glycidyl esters of polybasic aromatic and cycloaliphatic carboxylic acids. Examples include phthalic acid diglycidyl with more than 5.5 epoxide equivalents per kg with glycidyl esters of reaction products of 1 mol of an aromatic or cycloaliphatic dicarboxylic acid anhydride and ½ mol of a diol or 1/n mol of a polyol containing n hydroxyl groups or hexahydrophthalic acid diglycidyl esters which may optionally be substituted by methyl groups. Glycidyl compounds based on inorganic acid are also suitable, examples being triglycidyl phosphate, glycidyl ethers of hydroxyphenyl phosphoric acid esters, diglycidyl carbonate and tetraglycidyl titanate.

Cycloaliphatic epoxide compounds are also suitable. Examples of such compounds are compounds corresponding to the following formulae:

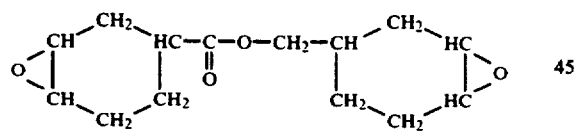

(3,4-epoxycyclohexyl methyl-3',4'-epoxycyclohexane carboxylate),

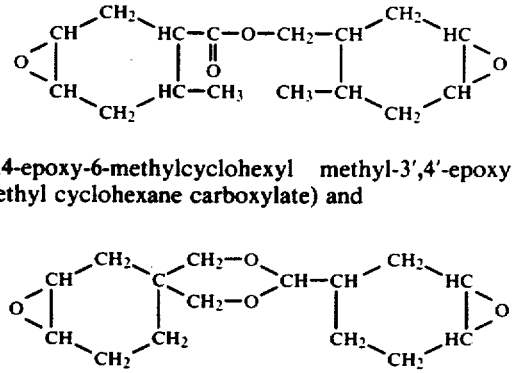

(3,4-epoxy-6-methylcyclohexyl methyl-3',4'-epoxy-6'-methyl cyclohexane carboxylate) and

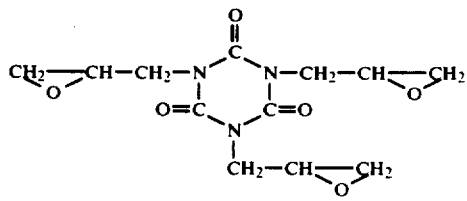

(3,4-epoxy hexahydrobenzal-3',4'-epoxycyclohexane-1',1'-dimethanol).

Suitable heterocyclic epoxide compounds are both the triglycidyl isocyanurate corresponding to the following formula:

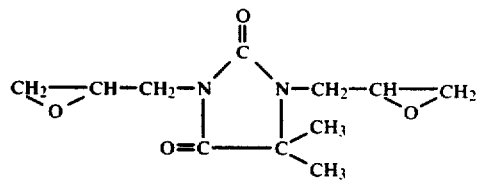

and also the N,N'-diglycidyl dimethyl hydantoin corresponding to the following formula:

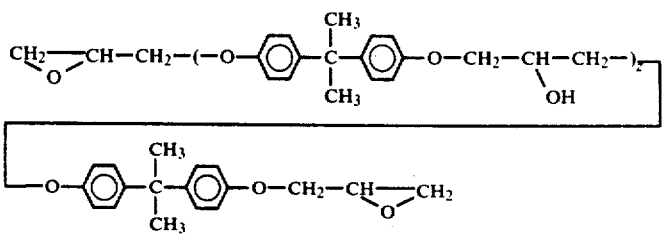

It is also possible to use mixtures of these cycloaliphatic and/or heterocyclic epoxide compounds.

Other suitable compounds are the polyglycidyl ethers of bis-(p-hydroxyphenyl)-dimethyl methane (bisphenol A) which corresponds to the average mean formula:

wherein z represents a low integer or fraction of from 0 to 2.

Other suitable diepoxides include, for example, glycerol diglycidyl ether, diglycidyl-N,N'-ethylene urea, diglycidyl-N,N'-propylene urea, N,N'-diglycidyl urea, N,N'-diglycidyl dimethyl urea and oligomers of these compounds, di, tri- or tetra-glycidyl acetylene diurea and oligomers of these compounds. Other epoxides which may be used in the present invention are known and may be found in Houben-Weyl, published by Eugn Muller, 1963, Vol. XIV/2, pages 462–538.

Other suitable epoxides are the epoxidation products of natural fats and oils, such as soya oil, olive oil, linseed oil, train oil. Epoxidation products of synthetic diesters or polyesters which contain fatty acids, such as oleic acid, linoleic acid, linolenic acid, ricinoleic acid and erucic acid are suitable.

Hydrophobic, water-insoluble and liquid monoepoxides and polyepoxides are particularly suitable. Examples of such monoepoxides and polyepoxides are: polyglycidyl ethers of polyhydric phenols, particularly of bisphenol A; polyepoxide compounds based on aromatic amines, particularly bis-N-epoxypropyl)-aniline, N,N'-dimethyl-N,N'-diepoxy propyl-4,4'-diaminodiphenyl methane and N,N'-diepoxy propyl-4-aminophenyl glycidyl ether; polyglycidyl esters of aromatic or cycloaliphatic dicarboxylic acids, particularly hexahydrophthalic acid diglycidyl ester and phthalic acid diglycidyl esters containing more than 5.5 epoxide equivalents per kg and also phosphoric acid triglycidyl ester.

A synopsis of commercially significant polyoxiranes may be found in H. Batzer and F. Lohse: Einfuhrung in die makromolekulare Chemie, Huthig & Wepf Verlag Basel, Heidelberg, 1976, pages 44 to 53.

Oxetanes suitable for use in the process according to the present invention are any organic compounds which contain at least one oxetane ring and which are optionally substituted by isocyanate or hydroxyl groups, but are otherwise substantially inert under the reaction conditions under which the oxetane/sulfonic acid addition takes place. Preferred oxetanes are monooxetanes corresponding to this definition having molecular weights of from 58 to 400.

Examples of suitable monooxetanes are: trimethylene oxide, 3,3-dimethyl oxetane, 3,3-diethyl oxetane, 3,3-dipropyl oxetane, 3,3-dibutyl oxetane, 3-methyl-3-dodecyl oxetane, 3-ethyl-3-stearyl oxetane, 3,3-tetramethylene oxetane, 3,3-pentamethylene oxetane, 3,3-pentamethylene oxetane, 2,6-dioxaspiro-(3,3)-heptane, 3-methyl-3-phenoxymethyl oxetane, 3-ethyl-3-phenoxymethyl oxetane, 3-methyl-3-chloromethyl oxetane, 3-ethyl-3-chloromethyl oxetane, 3-butyl-3-chloromethyl oxetane, 3-dodecyl-3-chloromethyl oxetane, 3-stearyl-3-chloromethyl oxetane, 3-methyl-3-bromomethyl oxetane, 3-ethyl-3-bromomethyl oxetane, 3-propyl-3-bromomethyl oxetane, 3-dodecyl-3-bromomethyl oxetane 3,3-bis-chloromethyl oxetane, 3,3-bis-bromomethyl oxetane, 3-methyl-3-hydroxymethyl oxetane, 3-ethyl-3-hydroxymethyl oxetane, 3-amyl-3-hydroxymethyl oxetane and 3,3-bis-hydroxymethyl oxetane, also ethers, esters and urethanes of these hydroxy oxetanes, such as 3-ethyl-3-methoxymethyl oxetane, 3-ethyl-3-butoxymethyl oxetane, 3-ethyl-3-dodecyloxy methyl oxetane, 3-ethyl-3-acetoxymethyl oxetane, 3-ethyl-3-stearoyloxy methyl oxetane, 3-ethyl-3-N-methyl carbamoylmethyl oxetane, 3-ethyl-3-N-chloroethyl carbamoylmethyl oxetane, 3-ethyl-3-N-phenylcarbamoylmethyl oxetane, 3-ethyl-3-N-dichlorophenyl carbamoylmethyl oxetane, 3-ethyl-3-N-stearyl carbamoylmethyl oxetane, 3,3-bis-phenoxymethyl oxetane, 3,3-bis-(4-chlorophenoxymethyl)-oxetane, 3,3-bis-(2,4-dichlorophenoxymethyl)-oxetane, 3,3-bis-(carbamoylmethyl)-oxetane and 3-phenoxymethyl-3-carbamoylmethyl oxetane. Other suitable oxetanes may be found in German Auslegeschrift No. 1,668,900, Columns 3 and 4.

It is, of course, also possible to use the oxetane analogues of the glycidyl derivatives mentioned above, for example 3-ethyl-3-acryloxy oxetane, 3-ethyl-3-methacryloxy oxetane, 3-methyl-3-trichloroacetoxy oxetane, 3-methyl-3-$\beta$-cyanoethoxy methyl oxetane, 3-ethyl-$\beta$-cyanoethoxymethyl oxetane and 3-ethyl-3-phenoxymethyl oxetane.

Among the dioxetanes and polyoxetanes which may be used in the present invention, the reaction products of 3-alkyl-3-hydroxymethyl oxetanes with dicarboxylic and polycarboxylic acids and with diisocyanates and polyisocyanates are of particular importance. The diethers and polyethers of hydroxyoxetanes derived from aliphatic, cycloaliphatic and aromatic diols and polyols are also eminently suitable.

The oxiranes are preferred to the oxetanes as starting materials for the process of the present invention. Particularly preferred oxiranes are ethylene oxide, propylene oxide, styrene oxide, 1,1,1-trichlorobutene-3,4-oxide and epichlorhydrin. The preferred oxetane is 3-hydroxymethyl-3-ethyl oxetane.

The quantitative ratio between the polyhydroxy compounds and the isocyanatosulfonic acid is generally selected in such a way that OH-functional products having molecular weights of less than 12,000, preferably less than 6000, are formed. Accordingly, a molar excess of hydroxy functional components is used, at least 1.5 OH-groups and SO$_3$H-groups being present per NCO-group. In the context of the present invention, NCO-groups are not only NCO-groups present in free form, but also dimerized NCO-groups present in the form of uretdione groups. It is particularly preferred to modify only part of the hydroxy functional compounds used as starting material with sulfonic acid groups. Up to 30 OH-groups and SO$_3$H groups may be used per NCO-group. An equivalent ratio of OH-groups to NCO-groups of from 2:1 to 20:1 is preferred.

The above-mentioned quantitative ratios apply largely to reactions which are carried out using diisocyanates and polyisocyanates and which lead directly to polyhydroxy compounds modified by sulfonic acid groups which, after reaction with oxiranes or oxetanes, give the polyhydroxy compounds of increased functionality according to the present invention.

However, it is also possible to use monoisocyanates containing from 1 to 3 sulfonic acid groups. These monoisocyanates may be used in sub-molar quantities or even in equivalent quantities with the starting hydroxy compounds. In the latter case, all the OH-functions are reacted with isocyanate groups. The polysulfonic acids obtained are subsequently reacted with oxiranes or oxetanes to form new polyhydroxy compounds. It is possible by adopting this procedure to obtain products whose OH-functionality is the same as in the starting compounds used, but whose reactivity is modified (e.g., reduced).

In principle, the reaction of the starting hydroxy compounds with the isocyanates containing sulfonic acid groups is carried out in known manner. In general, the hydroxy compounds are initially introduced and the isocyanate component is added with stirring. If the isocyanate is liquid, as is the case, for example, with partially sulfonated MDI-types, the components may readily be mixed and subsequently reacted at room temperature or even at slightly elevated temperature. In this case, the choice of the temperature is determined solely by the viscosity of the reaction mixture and by the required reaction time. In cases where solid isocyanatoaryl, mono- or poly-sulfonic acids are used, a suspension is initially formed during mixing and it is best to carry out the reaction at a temperature at which the solid isocyanate quickly passes into solution. Temperatures of from 40° to 180° C. are best used for this purpose, temperatures of from 60° to 120° C. being particularly suitable. Temperatures above 120° C. to about 200° C. are preferred, particularly in cases where only relatively low molecular weight polyhydroxy compounds are used, in order to prevent the reaction mixture from solidifying during the reaction. It is particularly preferred to use solid isocyanatosulfonic acids in the form of suspensions, pastes or moist powders using inert solvents, such as described in German Offenlegungsschrift No. 2,640,103.

It is also possible to use solid isocyanatosulfonic acids in the form of solutions in organic solvents, liquid esters of an inorganic or organic acid of phosphorus representing preferred solvents (German Offenlegungsschrift No. 2,650,172).

In addition, inert solvents, such as hydrocarbons, halogenated hydrocarbons, ethers, esters and ketones, may be added to the reaction mixture. However, it is preferred to carry out the reaction in the absence of solvents or by using only the small quantities of solvent used for making solid isocyanatosulfonic acids into pastes or solutions.

The reaction of the sulfonic acid groups introduced with oxiranes or oxetanes may be carried out either after the reaction of all the isocyanate groups in a second step or at the same time as or overlapping with the urethanization reaction. A simultaneous reaction is particularly appropriate in cases where the OH-groups of the starting components are primary, while the OH-groups emanating from the epoxide reaction are secondary. Under these conditions, there is only likely to be a minor reaction of the secondary OH-groups with isocyanate groups.

Accordingly, the reaction products of the present invention may also be produced by a one-pot process in which the hydroxy compounds, isocyanate component and the oxirane or oxetane are simultaneously mixed and reacted with one another. This process is also particularly appropriate in the case of substantially insoluble isocyanatosulfonic acids because the presence of oxygen heterocycles increases the rate of dissolution.

The oxiranes or oxetanes used in the process of the invention and the quantities in which they are employed are selected in such a way that the equivalent ratio of the epoxide or oxetane groups to sulfonic acid groups is from 0.2:1 to 5:1, and preferably from 0.6:1 to 2:1. Using an equivalent ratio of less than 1:1, the SO$_3$H-groups present are only partly esterified so that the products of the invention still contain free sulfonic acid groups. The hydrophilicity caused by these sulfonic acid groups may be varied through the above-mentioned equivalent ratio over the range of from 0.2:1 to 1:1. The epoxide or oxetane component may, of course, also be used in excess (for example where monoepoxides or monoxe- tanes are used) to guarantee a quantitative esterification of the sulfonic acid groups, or (where compounds containing more than one epoxide or oxetane group are used) to introduce free epoxide or oxetane groups into the products. Epoxide groups introduced in this way may be used, in particular, for subsequent reactions, such as trimerization of the isocyanate groups, oxazolidone formation or amine cross-linking.

Free sulfonic acid groups may also be completely or partly neutralized, for example using tertiary amines or inorganic bases.

Any excess of monoepoxide or monooxetane which may be used may, if desired, be removed from the product of the invention by distillation upon completion of the reactions.

The process of the invention is extremely easy to carry out and generally takes place at temperatures of from 0° to 190° C., and preferably from 20° to 140° C.

In cases where the process of the invention is carried out in batches, the mixture or reaction product of hydroxy component and polyisocyanate containing sulfonic acid groups is initially introduced into a stirrer-equipped vessel, preferably at room temperature, and the epoxide or oxetane is stirred in. The reaction is exothermic. In cases where the proportion of sulfonic acid groups amounts to more than about 10%, it may be advantageous to carry out the reaction at relatively low temperatures, for example from 0° to 20° C., and optionally to cool the reaction mixture. However, there is generally no need for such a measure because heating of the reaction mixture, for example to 140° C. or even higher, is not disadvantageous. In cases where rapidity of the reaction is important, i.e. a short reaction time, and in cases where epoxides and oxetanes liquid at room temperature or viscous isocyanates are used, it may be advantageous to carry out the reaction at elevated temperature, for example at temperatures of from 40° to 140° C. The temperature may be increased to about 190° C.

Where used, gaseous epoxides preferably are bubbled through the reaction mixture with stirring. The reaction is preferably carried out in the absence of solvents, although it may also be carried out in the presence of inert solvents, such as dichloroethane, chloroform, tetrachloroethane, trichlorofluoromethane, acetone, toluene and chlorobenzene.

A particularly marked increase in functionality may be obtained by using dioxiranes or polyoxiranes or the corresponding oxetanes, particularly in cases where the oxirane or oxetane is used in equivalent amounts to the sulfonic acid groups. Where such a procedure is adopted, it is readily possible to reach OH-functionalities of from 4 to 8. However, it is also possible to achieve a functionality of less than 4 where monoisocyanatoaryl monosulfonic acids and/or monofunctional alcohols are at least proportionately used.

Compounds particularly suitable for increasing functionality are also oxiranes and oxetanes containing OH-groups, for example glycidol, 3-methyl-3-hydroxymethyl oxetane and 3-ethyl-3-hydroxymethyl oxetane. Oxiranes or oxetanes will be preferred according to the required reactivity of the OH-functional short chain. Although oxetanes generally give primary OH-groups, the use of oxiranes generally leads to secondary or even tertiary OH-groups. Ethylene oxide yields a primary OH-group whereas glycidol simultaneously introduces a primary and a secondary OH-group within a short chain.

In cases where dioxiranes or polyoxiranes are used in molar excesses so that only some of the epoxy groups react with sulfonic acid groups, the polyhydroxy compounds obtained still contain free epoxy groups which may either be reacted with carboxylic acids or carboxylic acid anhydrides, for example, or may be used as reaction resins in epoxide chemistry.

The products of the present invention are valuable starting materials for the production of polyurethane plastics by the isocyanate-polyaddition process. They are suitable, for example, for the production of compact or cellular elastomers, flexible foams, semi-rigid foams and rigid foams, particularly when cross-linking density, flame resistance or degradability have to satisfy stringent requirements. Thus, the polyhydroxy compounds of the invention may be used for the production of upholstery materials, mattresses, elastic supports, car seats, damping materials, shock absorbers, construction materials, sound-damping insulating materials, moisture-absorbing materials, for example, in the hygiene sector, for the production of substrates for cultivating plants and for protection against heat and cold. The polyhydroxy compounds of the invention are particularly suitable for the production of inorganic-organic plastics for example by the processes described in German Pat. No. 2,310,559 and in German Offenlegungsschriften Nos. 2,227,147 and 2,359,608, and for surface coating, impregnation and bonding purposes.

One particular advantage of the hydroxy compounds of the present invention is the increased polarity thereof. Accordingly, these products, in contrast to pure polypropylene glycol ethers, are highly compatible with low molecular weight glycols, such as ethylene glycol, diethylene glycol, 1,4-butane diol and glycerol. Mixtures are homogeneous and stable in storage. The reaction of the polyhydroxy compounds of the invention with polyisocyanates containing sulfonic acid ester groups is particularly favorable for the production of polyaddition products having good flame resistance.

By virtue of the high polarity thereof, such polyisocyanates containing sulfonic acid or sulfonic acid ester groups are frequently incompatible with hydrophobic, long-chain polyethers, resulting in disintegration phenomena which in some cases may make a polyaddition reaction impossible. Where such polyethers are modified with sulfonic acid ester groups in accordance with the present invention, they are generally highly compatible with polyisocyanates containing sulfonic acid or sulfonic acid ester groups.

EXAMPLES

EXAMPLE 1

(a) Production of the isocyanatoaryl sulfonic acid:

1914 g (11 mols) of tolylene diisocyanate (80:20 mixture of 2,4- and 2,6-isomers) are reacted with stirring for about 20 hours at from 23° to 30° C. with 335 g (4.2 mols) of sulfur trioxide, resulting in the formation of a thickly liquid suspension of the dimeric tolylene diisocyanate monosulfonic acid in the tolylene diisocyanate. The sulfur trioxide is liberated from heated 65% oleum by means of a gentle stream of nitrogen and is directed, in gaseous form, diluted with nitrogen, onto the surface of the stirred isocyanate. The suspension obtained is diluted with 500 ml of toluene and filtered under suction. The solid residue is suspended twice with 500 ml of toluene and then filtered under suction. The toluene-moist product is run off. Yield: 1285 g, toluene content 23%, dry substance 990 g, corresponding to 93% of the theoretical yield.

The product is a slightly moist powder which may be handled very easily without giving off any dust. It may be handled easily, does not cake together and does not adhere to the spatula.

(b) Production of a polyether diol modified by sulfonic acid groups:

200 g (0.1 mol) of a linear difunctional polypropylene glycol having a molecular weight of 2000 are stirred at from 50° to 60° C. with 16.5 g (0.05 mol) of the product produced in accordance with (a). After 5 hours, a homogeneous melt free from NCO-groups has formed. Following the addition of 4.6 g (0.05 mol) of epichlorhydrin, the melt is stirred for 1 hour at 60° C. Viscosity at 25° C.: 2800 cP. Average functionality of the product: 3.

EXAMPLE 2

The procedure is as in Example 1, except that the epichlorhydrin is replaced by 8.5 g (0.025) of bisphenol A diglycidyl ether. Viscosity at 25° C: 50,000 cP. Average functionality of the product: 6.

EXAMPLE 3

240 g (0.12 mol) of a linear polypropylene glycol having a molecular weight of 2000 are stirred at 30° C. with 33 g (0.1 mol) of the product produced in accordance with Example 1(a). A white suspension is obtained, gradually changing into a clear liquid at 60° C. After 9.25 g (0.1 mol) of epichlorhydrin have been stirred in, the liquid is stirred for 30 minutes at from 40° to 50° C. Viscosity at 25° C.: 25,000 cP.

EXAMPLE 4

300 g (0.1 mol) of a trifunctional trimethylol propane-started polypropylene glycol having a molecular weight of 3000 are stirred at room temperature with 16.5 g (0.05 mol) of the product produced in accordance with 1(a). After heating to 60° C., a clear liquid is gradually formed into which 4.6 g (0.05 mol) of epichlorhydrin are stirred. Viscosity at 25° C.: 3400 cP.

EXAMPLE 5

In contrast to Example 4, the epichlorhydrin is stirred in immediately after the isocyanate. After stirring for 90 minutes at room temperature, the isocyanate has partially dissolved. The mixture is then heated to 60° C. and stirred at that temperature for 7 hours. A clear light brown liquid free from NCO-groups is obtained. Viscosity at 25° C.: 4500 cP. Light brown clear liquid. Average functionality: 5.

EXAMPLE 6

The procedure is as in Example 5, except that the epichlorhydrin is replaced by 3.7 g (0.05 mol) of glycidol. Pale yellow clouded liquid. Viscosity at 25° C.: 4500 cP. Average functionality: 6.

EXAMPLE 7

The procedure is as in Example 5, except that the epichlorhydrin is replaced by 5.8 g of 3-ethyl-3-hydroxymethyl oxetane. The mixture was stirred for 8 hours at 60° C., for 6 hours at 80° C., for 6 hours at 95° C. and for 2 hours at 120° C. 4 g of undissolved isocyanate were filtered off. Brown shimmering-green liquid. Viscosity at 25° C.: 4000 cP. Average functionality: 6.

EXAMPLE 8

200 g (0.2 mol) of a linear difunctional polypropylene glycol having a molecular weight of 1000 are stirred at 70° C. with 33 g (0.1 mol) of the product produced in accordance with Example 1(a) which is suspended in 30 g of toluene. After 1 hour, a clear melt has formed and after 4 hours no more NCO-groups are present (IR-spectrum). Toluene is distilled off in vacuo at 70° C. and the reaction product is stirred at 25° C. with 7.4 g (0.1 mol) of glycidol. Viscosity at 25° C: 11,000 cP. Average functionality of the product: 4. OH-number: 106. Acid number (ester splitting): 14.

EXAMPLE 9

The procedure is as in Example 8, except that 123 g (0.2 mol) of a linear polyethylene glycol having a molecular weight of 165 are used. Viscosity at 25° C: 30,000 cP. Average functionality: 4. OH-number: 136. Acid number (ester splitting): 26.

EXAMPLE 10

The procedure is as in Example 8, except that 80 g (0.2 mol) of octaethylene glycol are used. Viscosity at 25° C: 120,000 cP. Average functionality: 4. OH-number: 168. Acid number (ester splitting): 42.

EXAMPLE 11

20 g of the product obtained in accordance with Example 8 and 8 g of the product described in the following as polyisocyanate (A) are mixed, resulting in the formation of a homogeneous white-yellow paste. After 4 hours, a plastic high molecular weight mass has formed and, after another 2 hours, this mass has cross-linked into an elastomer. If the same test is carried out using 0.3 g of tin dioctoate, the mass has cross-linked only 2 hours after mixing. The cross-linked elastomer is homogeneous, tack-free and shows high tensile strength.

COMPARISON TEST

Example 11 is repeated using 20 g of the polypropylene glycol of molecular weight 1000 used as starting material in Example 8 and 8 g of the product described in the following as polyisocyanate (A). A two-phase mixture is obtained, of which the dark, heterogeneous isocyanate phase precipitates in the form of a sludge. The mixture is repeatedly stirred over a period of 5 hours, although phase separation also recurs after a few minutes. After 8 hours, the mixture is still liquid.

If the same test is carried out using 0.3 g of tin dioctoate, an inhomogeneous solid product having a crumbly appearance is formed in a highly exothermic reaction immediately after mixing. The product is tacky and has no strength.

POLYISOCYANATE (A):

Diisocyanatodiphenyl methane is distilled off from the crude phosgenation product of an aniline/formaldehyde condensate in such a quantity that the distillation residue has a viscosity of 50 cP at 25° C. (binuclear fraction: 68%, by weight; trinuclear fraction: 16%, by weight; proportion of more highly nuclear polyisocyanates: 16%, by weight; NCO-content: 32%, by weight). A mixture of sulfur trioxide and nitrogen is directed onto the surface of 3800 g of this product until 102 g of sulfur trioxide have been taken up by the isocyanate mixture. The product obtained has a viscosity of 120 cP and a sulfur content of 1.05%, 35.2 g of propylene oxide are added to 1850 g of this sulfonated polyisocyanate over a period of 30 minutes at room temperature. The mixture is then stirred for 4 hours at from 25 to 30° C. After 20 days, the thus-obtained polyisocyanate modified with sulfonic acid ester groups has a viscosity of 490 cP and a sulfur content of 1.03%.

What is claimed is:

1. A mixture of polyhydroxyl compounds containing at least two hydroxyl groups and at least one sulfonic acid ester group and having an average molecular weight of from 300 to 12,000, wherein at least one hydroxyl containing compound contains a urethane aryl sulfonic acid hydroxyalkyl ester group.

2. The compounds of claim 1, further comprising at least one hydroxyl functional long chain compound containing 6 to 400 chain members, at least one hydroxyl functional short chain containing 2 or 3 chain members which is attached to a branching point through a sulfonic acid ester residue, and at least one, at least trifunctional, aryl radical as said branching point.

3. The compounds of claim 2, wherein said at least one hydroxyl functional long chain contains 20 to 300 chain members.

4. A mixture of compounds having a molecular weight of 300 to 12,000 and containing a urethane aryl sulfonic acid hydroxyalkyl ester produced by reacting at 0 to 190° C.
   (a) compounds containing at least two hydroxyl groups and having a molecular weight of 62 to 10,000, with
   (b) aromatic isocyanatosulfonic acids; and subsequently reacting the reaction product of (a) and (b) with
   (c) oxiranes or oxetanes.

5. The compounds of claim 4, wherein the equivalent ratio of the total quantity of isocyanate groups including any isocyanate groups present in dimerized form to sulfonic acid groups is from 0.5:1 to 50:1, the equivalent ratio of the sum, of the hydroxyl groups in (a) and the sulfonic acid groups, to isocyanate groups is from 1.5:1 to 30:1 and the equivalent ratio of (c) to sulfonic acid groups is from 0.2:1 to 5:1.

6. The compounds of claim 4, wherein the equivalent ratio of (a) to (b) is from 2:1 to 20:1.

7. The compounds of claim 4, wherein the reaction product of (a) and (b) is reacted with an equivalent quantity of (c).

8. Compounds of claims 5 or 6 characterized as urethane aryl sulfonic acid hydroxyalkyl esters of the formula:

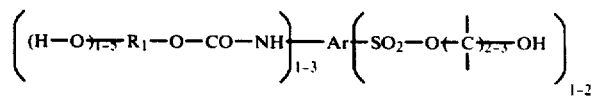

wherein
R₁ represents a 2- to 6-functional residue of a polyol; and

Ar represents a polyfunctional residue of an aromatic isocyanate.

9. The polyhydroxy compounds of claim 5 wherein said urethane aryl sulfonic acid hydroxyalkyl ester is of the formula:

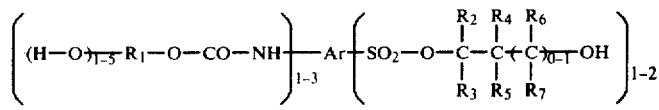

wherein $R_1$ and Ar are as defined in claim 8;

$R_2$ and $R_4$ represent H, $C_1$-$C_8$ alkyl, $C_6$-$C_{14}$ aryl, a residue of an epoxide, —$CH_2$—X, $CH_2$—O—CO—$R_9$ or an aliphatic $C_1$-$C_8$ alkyl radical containing epoxide groups;

$R_3$, $R_5$, $R_6$ and $R_7$ represent H, $C_1$-$C_8$ alkyl or $C_6$-$H_{14}$ aryl;

$R_8$ and $R_9$ represent $C_1$-$C_8$ alkyl or $C_6$-$H_{14}$ aryl; and X represents OH, Cl, Br or CN.

10. The polyhydroxyl compounds of claim 4, wherein there is at least one hydroxyl functional long chain containing 6 to 400 chain members, at least one hydroxyl functional short chain containing 2 or 3 chain members which is attached to a branching point through a sulfonic acid ester residue, and at least one, at least trifunctional, aryl radical as said branching point.

11. The polyhydroxyl compounds of claim 7, wherein said at least one hydroxyl functional long chain contains 20 to 300 chain members.

12. The polyhydroxyl compounds of claim 4 corresponding to the formula:

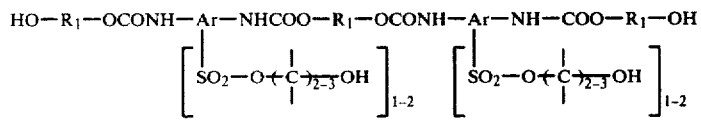

wherein $R_1$ represents a from 2- to 6-functional residue of a polyol; and

Ar represents a polyfunctional residue of an aromatic isocyanate.

13. The polyhydroxyl compounds of claim 12 corresponding to the formula:

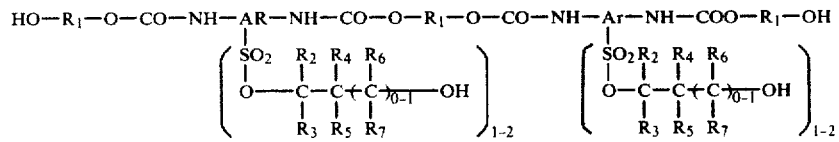

wherein $R_1$ and Ar are as defined in claim 8.

14. A process for producing a mixture of polyhydroxy compounds containing at least two hydroxyl groups which is in the form of a urethane aryl sulfonic acid hydroxyalkyl ester and having a number average molecular weight of 300 to 12,000, comprising:

reacting at 0° to 190° C., (A) compounds containing at least two hydroxyl groups and having a molecular weight of 62 to 10,000; with (B) aromatic isocyanatosulfonic acids; and subsequently reacting the reaction product of (A) and (B) with (C) oxiranes or oxetanes.

15. The process of claim 14, wherein the equivalent ratio of the total quantity of isocyanate groups (including dimerized isocyanate) to sulfonic acid groups is from 0.5:1 to 50:1, the equivalent ratio of the sum of the hydroxyl groups in (A) and the sulfonic acid groups to isocyanate groups is from 1.5:1 to 30:1 and the equivalent ratio of (C) to sulfonic acid groups is from 0.2:1 to 5:1.

16. The process of claim 14, wherein (A) is reacted with a sub-molar quantity of (B).

17. The process of claim 16, wherein (A) and (B) are reacted in admixture with additional polyisocyanates.

18. The process of claim 15 wherein the reaction temperature is from 20° to 140° C.

19. The process of claim 15, wherein Component (B) is selected from the group consisting of 2,4-diisocyanatotoluene, 2,6-diisocyanatotoluene and mixtures thereof.

20. The process of claim 15, wherein Component (C) is selected from the group consisting of ethylene oxide, propylene oxide, epichlorohydrin, glycidol, 3-methyl-3-hydroxy methyl oxetane, 3-ethyl-3-hydroxy methyl oxetane, 1,1,1-trichlorobutene-2,3-oxide, 1,4-dibromobutene-2,3-oxide and the bis-glycidyl ether of bisphenol A.

* * * * *